United States Patent [19]
Vandermeerssche et al.

[11] Patent Number: 5,835,621
[45] Date of Patent: Nov. 10, 1998

[54] ABRASION ANALYZER AND TESTING METHOD

[75] Inventors: Gaston A. Vandermeerssche, 9240 N. Sleepy Hollow La., Milwaukee, Wis. 53217; Stephen M. Dicke, Evanston, Ill.

[73] Assignee: Gaston A. Vandermeerssche, Milwaukee, Wis.

[21] Appl. No.: 945,061

[22] Filed: Sep. 15, 1992

[51] Int. Cl.$^6$ ..................................................... G06K 9/00
[52] U.S. Cl. ........................................... 382/141; 382/218
[58] Field of Search .................................... 382/50, 34, 8, 382/22, 30, 44, 45, 46, 270, 218, 141, 199, 209, 293, 295, 296

[56] References Cited

U.S. PATENT DOCUMENTS

| | | | |
|---|---|---|---|
| 3,583,216 | 6/1971 | Milewski | 73/105 |
| 3,987,241 | 10/1976 | Lloyd et al. | 358/106 |
| 4,075,604 | 2/1978 | Degasperi | 340/146.3 |
| 4,125,858 | 11/1978 | Hounsfield | 382/6 |
| 4,129,853 | 12/1978 | Althauser et al. | 385/50 |
| 4,318,082 | 3/1982 | King | 340/146.3 |
| 4,435,834 | 3/1984 | Pauli et al. | 382/7 |
| 4,472,736 | 9/1984 | Ushio et al. | 358/75 |
| 4,507,953 | 4/1985 | Vandermeerssche | 73/7 |
| 4,509,826 | 4/1985 | Araghi | 350/286 |
| 4,529,184 | 7/1985 | Vandermeerssche | 269/48.1 |
| 4,561,103 | 12/1985 | Horiguchi | 382/1 |
| 4,608,854 | 9/1986 | Vandermeerssche | 73/7 |
| 4,878,753 | 11/1989 | Nestmeier | 356/237 |
| 4,941,192 | 7/1990 | Mishima et al. | 382/54 |
| 5,010,578 | 4/1991 | Siener et al. | 382/8 |
| 5,019,918 | 5/1991 | Kubota et al. | 358/473 |
| 5,113,454 | 5/1992 | Marcantonio et al. | 382/27 |

FOREIGN PATENT DOCUMENTS

| | | |
|---|---|---|
| A 0 078 708 | 5/1983 | European Pat. Off. |
| A 0 456 126 | 11/1991 | European Pat. Off. |
| 53-5536 | 1/1978 | Japan ............ G06K 9/00 |
| 344542 | 2/1991 | Japan ............ G01N 21/88 |
| WO A 91 20054 | 12/1991 | WIPO |

OTHER PUBLICATIONS

Patent Abstracts Of Japan, vol. 10 No. 149 (P–461 May 30, 1986 JP A 61 003 005.

Patent Abstracts Of Japan, vol. 14 No. 400 (P–1098) Aug. 29, 1990 JP A 02 151 982.

"The Pressure Is On . . . The Packaging Professional Is Facing New Challenges!", *Journal of Packaging Technology*, vol. 1, No. 3, Jun. 1987.

"Using The CAT To Test The Rub", presented at the 40th Annual Conference of the Technical Association of the Graphic Arts in May 1988.

"Standard Test Method For Abrasion Resistance of Printed Matter By The GA–CAT Comprehensive Abrasion Tester" ASTM Standard D 5181–91, Dec. 1991.

Gonzalez & Woods: "Digital Image Processing" 1992: Addison–Wesley. pp. 318–320.

*Primary Examiner*—Phuoc Tran
*Attorney, Agent, or Firm*—Quarles & Brady

[57] ABSTRACT

A specimen to be tested for resistance to abrasion is optically scanned prior to abrasion to produce a first array of pixels. The specimen then is abraded under controlled conditions and scanned again after abrasion to produce a second array of pixels. The sections of the two arrays which relate to the specimen are registered to each other. Corresponding pixels for the specimen in each array are compared to produce plurality of values indicating the difference between the pixels. The difference values are used to quantify the abrasion in various defined regions of the specimen. The quantifying employs the difference values to determine an average magnitude, a mean square energy, and an average voltage of the abrasion. A contour map of the specimen is displayed to graphically show the degree of abrasion in the regions.

20 Claims, 3 Drawing Sheets

ABRASION ANALYZER AND TESTING METHOD

BACKGROUND OF THE INVENTION

The present invention relates to testing printed or coated materials for resistance to abrasion; and more particularly to an apparatus for producing abrasion on a surface under defined conditions and analyzing the surface to quantify the amount of abrasion produced.

Printed items, such as magazines covers, books, catalogs and product containers, are usually packed in contact with one another when being shipped by rail or truck. During shipment the items are exposed to various types of vibrations which causes the surfaces of adjacent items to rub together. This rubbing often smears the printing producing serious consequences such as making bar codes and instructions for product use unreadable. Not only will the ink be smeared or rubbed off, the substrate upon which the ink is deposited can be abraded to the point where holes are formed. Extreme abrasion may result in containers leaking during shipment. Even when the printed surface is treated with an over coat for protection, the abrasion may adversely affect the printing.

Printing inks and over coatings differ widely in resistance to abrasion. It is therefore desirable for a printer to be able to test such resistance in advance of shipping printed materials. This enables the printer to determine the ink which is best suited for the particular material being printed and for distance to which the printed material will be shipped.

U.S. Pat. No. 4,507,953 discloses a machine for testing the abrasion resistance of coatings. Although this original machine was developed to test the abrasion resistance of coatings applied to beverage cans, subsequent U.S. Pat. No. 4,608,854 teaches a holder for testing flat specimens. The testing machine permitted the amount of rubbing between two specimens to be carefully controlled and duplicated using specimens printed using different inks and over coatings. Alternatively, a "receptor" having a surface with a known abrasive characteristic, was placed in the testing machine against the printed surface to be analyzed. The testing machine was able to replicate the motion which occurred during transportation of printed objects and thereby produce abrasion of the coated or printed surface which was likely to occur during transportation.

Although the previous testing equipment could accurately replicate such abrasion, a human had to visually inspect the abraded sample to determine whether the degree of abrasion would be acceptable to the end user of the printed material. Such inspection was very subjective. Not only could various individuals evaluate the same sample differently, the same individual might not consistently evaluate the same sample. It was also difficult to accurately compare abraded samples having identical images printed with different inks. Thus a need arose for an objective process by which to quantify the degree of abrasion in order to compare abraded samples in order to select a printing ink or over coating best suited to a particular application.

SUMMARY OF THE INVENTION

In order to test a specimen, such as a printed or a coated sheet, for resistance to abrasion, a scanner generates an image of the specimen prior to abrasion. The image is formed by a first array of pixels which is stored in a memory. Next the specimen is abraded under a controlled set of conditions. Preferably the specimen is placed in contact with another like specimen or a receptor and then between block-like members having curved end surfaces to form a test assembly. The test assembly is positioned on a platform with the curved end surfaces of the block-like members abutting the platform. Regulated pressure is applied to maintain the assembly sandwiched together and against the platform. The platform is vibrated with the magnitude of vibration being controlled to produce a desired degree of rubbing between the specimens or between the specimen and the receptor.

The specimen is removed from the assembly and scanned again to generate another image that is formed by a second array of pixels If desired, both arrays of pixels may be corrected for non-uniformity in the response of the scanner. Sections of the two arrays which represent the specimen are compared to determine the extent of the abrasion. Specifically, corresponding pixels in each array are selected and the difference between the magnitude of the selected pixels is calculated to produce a set of difference values.

The set of difference values is evaluate to quantify the abrasion of the specimen regions of the second array of pixels wherein each region is defined by array row addresses Y1 and Y2, and by array column addresses X1 and X2. In the preferred embodiment the difference values are used to calculate the parameters of average magnitude, mean square energy, and average voltage for the specimen. These parameters are defined by the following expressions:

$$\text{Average Magnitude} = \left( \frac{1}{MN} \sum_{i=Y1}^{Y2} \sum_{j=X1}^{X2} |\Delta_{ij}| \right) - TN$$

$$\text{Mean Square Energy} = \left( \frac{1}{MN} \sum_{i=Y1}^{Y2} \sum_{j=X1}^{X2} \Delta_{ij}^2 \right) - TN' - (2(MPV)\sqrt{TN'})$$

$$\text{Average Voltage} = \sqrt{\text{Mean Square Energy}}$$

where M is the number pixels in each row of the region, N is the number pixels in each column of the region, $\Delta_{i,j}$ is the difference between corresponding pixels in each array, TN is the mean absolute deviation of the thermal noise, TN' is the mean square deviation of the thermal noise and MPV is the mean pixel value. Depending upon the performance of the image scanner and the degree of accuracy desired the thermal noise components may be eliminated from these expressions. The first and second arrays of pixels can be subdivided into a series of smaller groups of pixels associated with various regions of the specimen. The difference values between the pixels in the groups also are used to derive the three parameters for each group to quantify the amount of abrasion in the corresponding region of the specimen.

A principal object of the present invention is to provide a process and apparatus for objectively determining the amount of abrasion of a specimen.

DESCRIPTION OF THE PRESENT INVENTION

Figure 1:
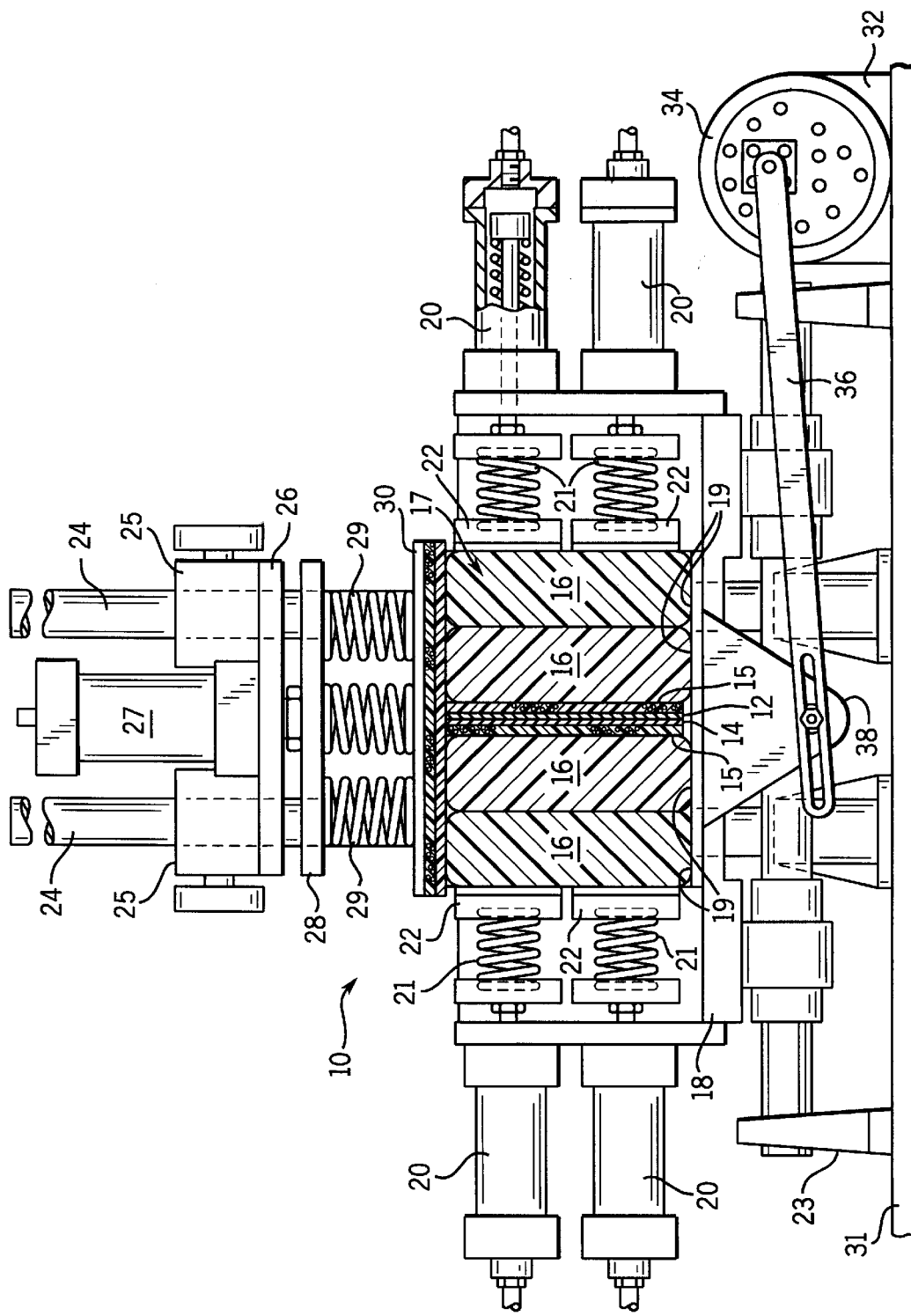
FIG. 1 illustrates an apparatus for producing abrasion on a flat surface.

With initial reference to FIG. 1, a machine 10 is capable of producing abrasion on a flat surface under a variety of predefined conditions. Specifically, the machine 10 can be configured to vary the pressure applied to the surface being tested as well as the rubbing applied to that surface. An apparatus of this type is illustrated and described in detail in U.S. Pat. Nos. 4,507,953 and 4,608,854, the descriptions in which are incorporated herein by reference.

A specimen sheet 12 having the coated or printed surface to be tested is placed upright against another 14. Alternatively the testing process can be used to determine the resistance to abrasion of an uncoated container material, such as a type corrugated cardboard. The other sheet 14 may either be a duplicate of the specimen sheet 12 or a receptor sheet having a surface within a known abrasion coefficient. Sheets 12 and 14 are sandwiched between two pads 15 which in turn are sandwiched in the middle between four blocks 16.

The assembly 17 of sheets 12 and 14, pads 15 and blocks 16 is mounted on a platform 18 of the testing apparatus 10. The ends 19 of the blocks 16 in contact with the platform 18 are curved. Horizontal force is applied to the assembly by a pair of horizontally oriented hydraulic cylinders 20 located on each side of the test machine 10. The piston rods of the cylinders 20 push springs 21 against vertical plates 22 on each side of the assembly 17, thereby exerting horizontal force that presses the two sheets 12 and 14 together. By extending and retracting the piston rods, the springs 21 are compressed or released to vary the amount of pressure applied to the sheets 12 and 14.

A pair of upright standards 24 rise from the floor 31 of the machine behind platform 18. The standards 24 mount a pair of releasable clevises 25 which in turn support a horizontal mounting plate 26 on which a vertical hydraulic cylinder 27 is fastened. The piston of hydraulic cylinder 27 engages an intermediate plate 28 to compress springs 29 against a top pressure plate 30 in contact with the top of assembly 17. Varying the position of the vertical piston changes the downward force exerted by springs 29 that pushes assembly 17 against the platform 18.

The platform 18 is supported from the floor 31 of the apparatus by a pair of supports 23, one of which being visible in FIG. 1. Also mounted on the floor 31 is an electric motor 32 which rotates an eccentric plate 34. One end of a lever arm 36 is pivotally attached to the face of the eccentric plate 34. The point of attachment is adjustable as is the speed of electric motor to provide varying degrees of movement of the lever arm 36. The opposite end of the lever arm 36 is provided with a longitudinal slot which receives a threaded bolt that extends into an opening in a bracket 38 depending from the horizontal platform 18. Movement of the lever arm 36 by motor 32 vibrates the platform 18. As the platform vibrates the curved ends 19 cause the four blocks 16 to swing or rock back and forth which rubs the two sheets 12 and 14 against each other. This action causes abrasion of the sheets. For enhanced the rocking action, pistons of the two upper horizontal hydraulic cylinders 20 are retracted so as not to exert force on the assembly 17.

The force applied by the hydraulic cylinders and springs can be varied by adding or releasing hydraulic fluid in each cylinder. Also, the speed of the motor 32 can be adjusted to vary the cycle of vibration. The two sheets 12 and 14 will rub against each other as the platform 18 is vibrated and the pressure applied by the various cylinders will simulate the stacking and packaging of the sheets under test. Apparatus 10 is used to replicate the abrasive effects of motion during transportation of coated sheets.

Figure 2:
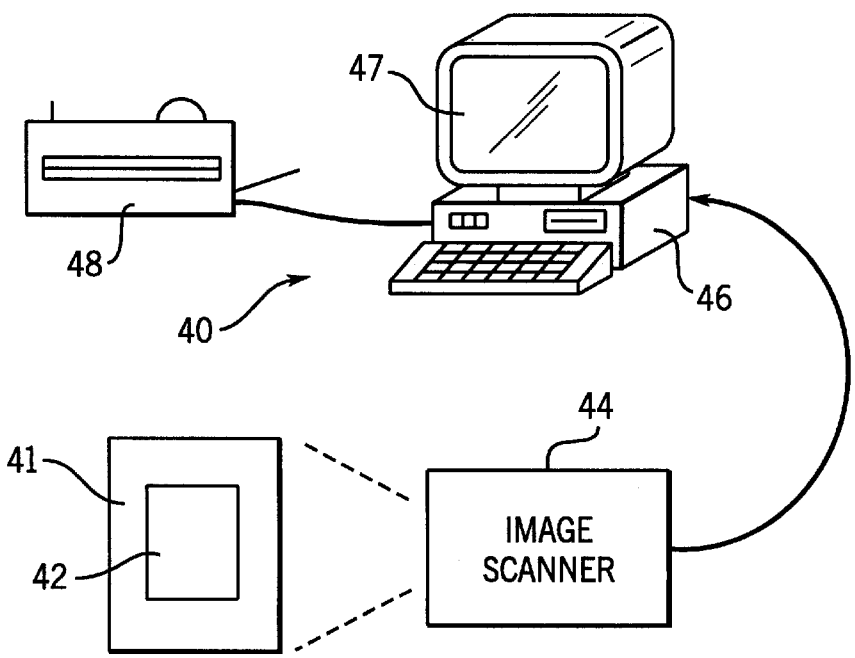
FIG. 2 is a block diagram of a system for visually analyzing an image which has been abraded by the apparatus in FIG. 1.

Once a specimen sheet 12 has been abraded by the apparatus 10, either it or the receptor 14 is evaluated optically by an image analyzer 40 shown in FIG. 2 to determine the amount of abrasion of the specimen sheet 12. During the evaluation the specimen sheet 12 or receptor 14 is referred to as a "test sample." The analyzer 40 optically scans the test sample before and after abrasion in apparatus 10 to have two images of the sample to compare for abrasion. However, when a receptor is being analyzed, a master reference image of that type of receptor may be used as the before image in place of scanning the actual receptor used in the testing, since all receptors of a given type are virtually identical. In preparation for the scanning, the test sample 42 is placed against a contrasting white or black background matte 41 and the operator enters the matte color into a personal computer 46. The combination of the matte 41 and the test sample 42 is scanned by an image scanner 44 that is designed to provide image information to a personal computer. For example, the image scanner 44 may comprise an Epson-300C model color scanner, a Logitech model GS256 hand-operated scanner or a video camera. The image analysis will be described in terms of a monochrome image. However, when a color scanner is used, each color component image (e.g. red, green and blue; or luminance and chrominance) is analyzed separately in the same manner as a monochrome image. The image scanner 44 produces a two dimensional array (rows and columns) of digital pixels representing the image being scanned. The series of image pixels are sent to and stored within a memory of the personal computer 46, (as used herein this memory includes a hard disk drive). In this manner, images of the test sample 42 before and after abrasion by apparatus 10 are stored in the personal computer 46. Once stored the image of the test sample can be displayed on the monitor of the personal computer. As will be described, the personal computer 46 analyzes these images and produces results quantifying the degree of abrasion which results can be displayed on a computer monitor 47 or printed by printer 48.

The characteristics of some types of image scanners non-uniformly affect pixels in different sections of the image. Many scanner employ a number of photodetectors to sense the light from the test sample 42 and each photodetector has different light response characteristics. In addition the response of a photodetector is a function of its temperature which changes during an image scan This effect introduces thermal noise into the signal from the photodetector. In order to be able to compare images acquired before and after abrasion, compensation should be provided for the non-uniformity of the photodetector response.

To calibrate the analyzer 40, a standard reference sheet is scanned by the image scanner 44 to produce an array of pixels which is stored in the computer 46. For example, this reference sheet may be a receptor sheet or a standard gray card used in photography. As the reference sheet has uniform gray scale and color, all of the pixels of its image should be identical. However, the different responses of the photodetectors and the effects of thermal noise will cause a variation among the pixels.

Figure 3:
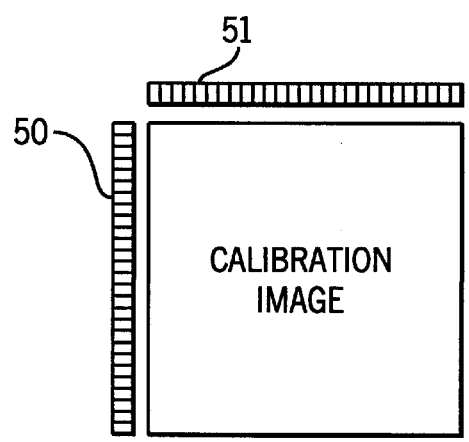
FIG. 3 graphically depicts the production of calibration data for the system in FIG. 2.

The compensation for detector response variation requires a correction factor for each pixel location in the image. Although the entire calibration image could be stored in the computer 46 for this purpose, that would require a significant amount of memory. In order to conserve memory, the calibration image preferably is converted into a separable form. This conversion is graphically depicted in FIG. 3 and produces vertical and horizontal correction vectors 50 and 51. The vertical vector 50 is produced by separately summing the pixel values in each row of the calibration image and dividing each sum by the mean pixel value for the entire calibration image thereby deriving an average sensitivity value. The vertical vector 50 is a one-dimensional array of these average sensitivity values for every row. The horizontal vector 51 is a single dimension array of average sensitivity values for every column of pixels in the calibration image and is produced in a similar manner to the vertical vector 50. As will be described, these vectors 50 and 51 are utilized to calculate a correction value for each pixel location in an image being analyzed.

The calibration image also is used to produce a correction factor for the thermal noise. An average value for all of the pixels in the calibration image is determined. Then the mean absolute deviation from that average and the mean square deviation are calculated using well known statistical techniques. The use of these correction factors will be described subsequently. Once both types of correction values have been determined, the calibration image can be deleted from memory.

After image analyzer 40 has been calibrated, it can be used to evaluate abrasion. As noted previously, the evaluation consists of comparing images of the test sample 42 before and after abrasion. The initial steps of the image processing are the same for the before and after images.

Figure 4:
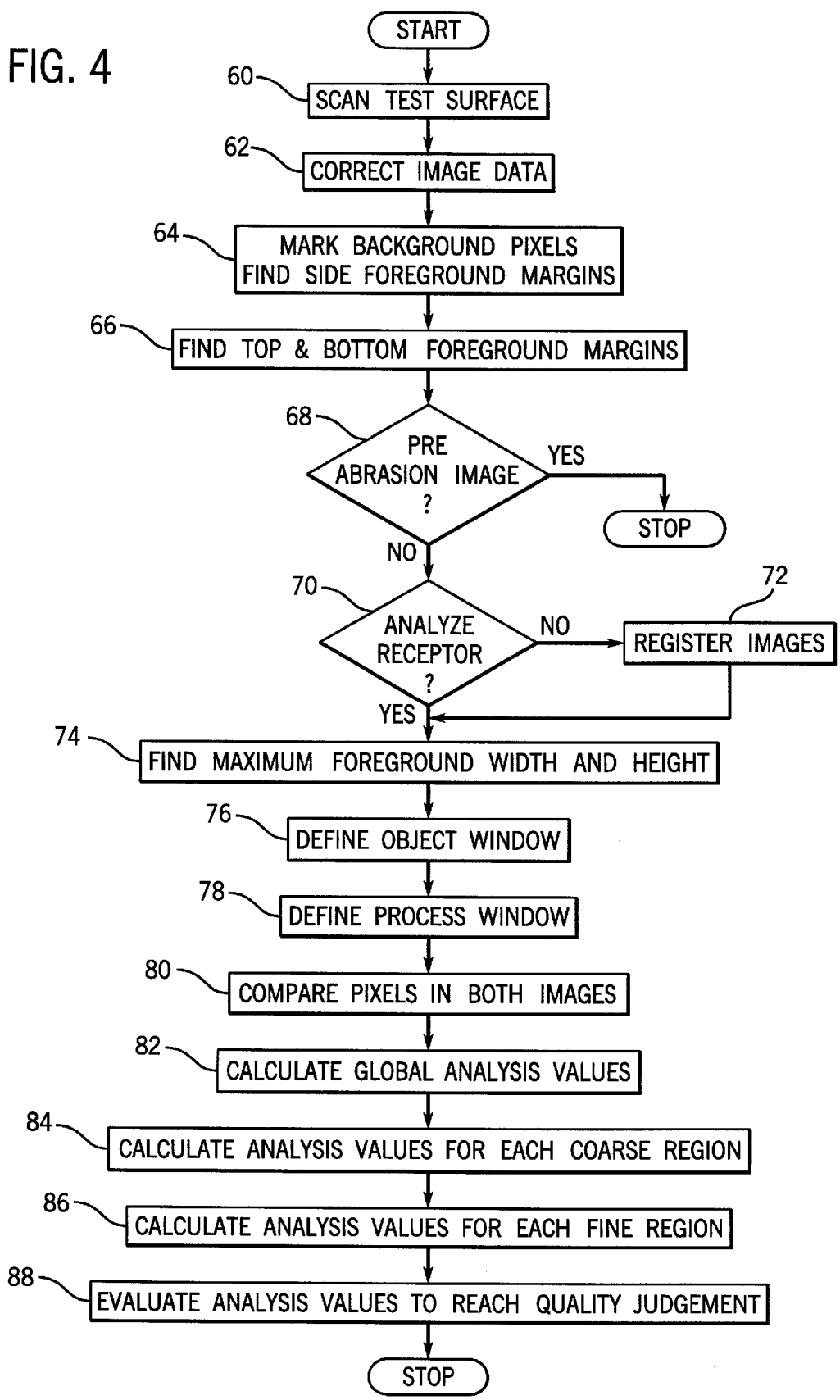
FIG. 4 is a flowchart of the process by which an abraded image is analyzed.

With reference to FIG. 4, the image processing begins by scanning the surface of the test sample 42 at step 60. The resultant test sample image consisting of the two-dimensional array of pixels is stored within the memory of personal computer 46. The image is then corrected utilizing the separable data produced during the calibration process. The correction proceeds by obtaining each pixel of the test sample image and adjusting its digital value based on the averages obtained from the reference separable. To do so, the digital value of the pixel is divided by the product of the average in the vertical vector 50 for the row in which the pixel is located and the average in the horizontal vector 51 for the column of the image in which the pixel is located. This produces a corrected pixel value which is stored in the computer memory to form a corrected test sample image at step 62.

At step 64, each pixel of the corrected test sample image is inspected to identify background pixels that represent the matte 41 and foreground pixels that were produced by the test sample. Because of the high degree of contrast between the matte 41 and the test sample 42, the matte typically are represented by pixels having numerical values at one end of the range of digital pixel values. For example, depending upon whether a white or black matte is used, the background pixels either will be substantially zero or substantially 255 for pixel values represented by eight binary digits. A pixel is considered to be part of the foreground if at least a given amount of difference exists between its value and the nominal value (0 or 255) of matte pixels. During the pixel classification process the background pixels in the test sample image are set to a value of zero. In doing so, the computer 46 steps through the test sample pixel array row by row For a given row, the computer starts at the right end and moves inward checking the pixel values and setting the pixels to zero until a foreground pixel is found. The column address of this first foreground pixel is saved in a margin table as indicating part of a right side margin of the image foreground. If the other end of the pixel array row is reached without finding a foreground pixel, the whole row is considered to be part of the background and the right margin table entry is set to −1. Then, the personal computer 46 proceeds to the left end of the pixel array row and moves inward setting the background pixels to zero until a foreground pixel is found. The column address of this foreground pixel is saved in the margin table as indicating the left side margin of the image foreground. The computer 46 then inspects the pixels between the right and left side margins and any foreground pixels with a zero value are set to one. Every row of the test sample pixel array is processed in this way. The result of step 64 is a revised pixel array for the test sample image in which the background pixels have a value of zero and the foreground pixels have values in the range 1–255. Alternatively, a separate binary image may be created in which the foreground pixel bits are assigned one logic level and the background pixel bits are designated by the other logic level.

The revised test sample image is inspected to locate the top and bottom margins of the foreground portion at step 66. This involves inspecting the array of pixels column by column to find the upper and lower transition between zero and non-zero pixels. The result is another data table that is stored within the personal computer memory containing the pixel row locations of the top and bottom foreground margins for each column of the test sample image array. The margin tables produced in steps 64 and 66 are maintained for the before and after abrasion test sample images. The margin information is useful to determine the degree to which the test sample 42 is skewed in the image. Ideally, the left and right side margins should each fall within a single pixel column, and each of the top and bottom margins should fall on a single pixel row. However, it is virtually impossible to achieve this type of registration and some skew will exist.

At step 68, a determination is made whether the operator of the computer has indicated that the image being processed is of the test sample 42 prior to abrasion. If this is the case, the program execution terminates.

When the analysis is being conducted on a post abrasion test sample image, the program execution continues at step 70. At this juncture, a determination is made by the personal computer 46 whether the image being analyzed was produced by scanning the specimen sheet 12 or by scanning the surface of a receptor that was used to perform the abrasion. If a receptor is used, particles of the ink or coating adhere to the receptor and thus the receptor surface will be discolored in proportion to the degree of abrasion. Whether the actual test surface or the surface of a receptor is being analyzed, is part of the information which the user enters via the keyboard into the personal computer 46 prior to image scanning. If the specimen sheet 12 is being analyzed, the before and after images must be registered so that corresponding pixels in the two stored images correspond to the same point on the sheet. When a receptor is being analyzed, since the surface of the receptor before abrasion is uniform, all of its pixels should be virtually identical and precise pixel registration is not required.

Therefore, if the specimen sheet 12 is being analyzed, an additional step 72 is executed to register the two test sample images. A conventional process for doing so is executed by the personal computer. For example, the equation for the upper margin and left margin of the foreground in the before and after test sample images is calculated. Then the after image data is translated in the storage array so that the pixel at the intersection of the upper and left margins coincides with the location of the pixel in the before image where the left and right margins intersect. The after test sample image then is rotated until the left and right margins are aligned with those margins of the before image. The registered after test sample image is stored in the computer in place of the unregistered after image. Alternatively, registration can be performed by placing a reference mark on the matte 41 and registering the reference marks in the before and after test sample images.

The margin information for the after abrasion image is inspected at step 74 to find the row in which the foreground has the maximum width (i.e. the largest number of pixel columns between side margins). This number of pixel columns is stored within the personal computer memory as the maximum foreground width. The maximum foreground height in terms of pixels rows is found by inspecting the top and bottom margins and its value is stored in the memory of the personal computer.

An "object window" then is defined for the before and after images of the test sample at step 76. For example, the after abrasion image is inspected by the personal computer 46 to find the first row from the top in which the foreground has the width equivalent to at least eighty percent of the maximum foreground width found at step 66. This defines the upper boundary of the object window. A similar process is performed to find the lower boundary of the object window by going upward row by row from the bottom of the binary image until a row is found in which the foreground portion is at least eighty percent of the test sample width. Similarly, the computer 46 searches column by column from opposite sides of the after image to locate left and right object window boundaries defined by the first column from each side at which the foreground is at least eighty percent of the maximum foreground height found at step 66. These boundaries define the object window that contains only pixels corresponding to the test sample 42, thereby avoiding the need to analyze pixels which clearly are part of the background.

A problem sometimes encountered when using apparatus 10 in FIG. 1 to produce abrasion is that the edge of each sheet 12 or 14 significantly abrades the other sheet. This edge abrasion effect typically is not representative of abrasion which occurs during transportation of the coated material. Therefore, in order to exclude the edge abrasion of the test sample 42 from being analyzed, a "process window" is defined by shrinking the object window at step 78. In essence, the margins of the object window are moved inward toward the center of the image by a fixed number of pixels. Only the pixels within the process window will be analyzed for abrasion effects, thereby eliminating pixels representing edge abrasion.

Then at step 80, corresponding pixels in each of the before and after test sample images are compared. Ideally, in the absence of abrasion, the corresponding pixel in the after image has the same numerical value as in the before image. The difference between every pair of corresponding pixels then is calculated and the difference value $\Delta$ is stored in a two-dimensional array in the computer memory. The magnitude of the difference value $\Delta$ indicates the degree of abrasion at that location on the specimen sheet 12.

From the array of pixel difference values, the image analyzer 40 produces numerical values for three parameters indicating the magnitude of the abrasion which occurred on the specimen sheet 12. Values for these parameters are determined for a given region of the image that is defined by array row addresses Y1 and Y2, and by array column addresses X1 and X2. The three parameters are average magnitude, mean square energy, and average voltage and are defined according to the following equations:

$$\text{Average Magnitude} = \left( \frac{1}{MN} \sum_{i=Y1}^{Y2} \sum_{j=X1}^{X2} |\Delta_{ij}| \right) - TN$$

$$\text{Mean Square Energy} = \left( \frac{1}{MN} \sum_{i=Y1}^{Y2} \sum_{j=X1}^{X2} \Delta_{ij}^2 \right) - TN' - (2(MPV)\sqrt{TN'})$$

$$\text{Average Voltage} = \sqrt{\text{Mean Square Energy}}$$

where M is the number pixels in each row of the region being evaluated, N is the number pixels in each column of that region, $\Delta_{i,j}$ is the difference between corresponding pixels, TN is the mean absolute deviation of the scanner thermal noise, TN' is the mean square deviation of the scanner thermal noise, and MPV is the mean pixel value in the image region.

At step 82, these equations are solved using all of the pixels within the process window to provide a global evaluation of the test sample 42. In this case, N in the equations is the number of pixels in the process window. The global values for these parameters represent an overall evaluation or analysis of the specimen sheet 12.

In addition, the image is subdivided into a matrix of smaller regions, each of which is evaluated individually by producing a separate set of values for the three parameters for each region. At step 84, the test sample image array is divided into 16 by 16 pixel coarse regions. The personal computer 46 analyzes each of these smaller sub-regions by deriving values for the average magnitude, average magnitude, means square energy and average voltage for the 256 pixels in each coarse sub-region. At step 86, the image is divided into a matrix of eight by eight pixel fine regions and the three parameters are calculated for each of these finer sized regions. The size of each coarse and fine region can be defined by the user prior to processing. The parameter values for each of the coarse and fine sub-regions are stored in tables within the computer 46.

The parameter values may be printed on printer 48 as a two-dimensional matrix which corresponds to the areas of the image represented by each of the coarse sub-regions. The fine sub-regions are relatively small and data for them is not easily perceived by the user. From this data, an image contour map is constructed and printed in which different colors represent sections of the test sample having various degrees of abrasion.

At step 88, the computer then analyzes the tables of parameter data to produce a relative qualification of the post abrasion specimen sheet 12 as being excellent, good, fair or poor, for example. Such an evaluation can either be printed by the printer 48 or displayed on the monitor 47. The before and after images of the test sample can be displayed on the monitor 47. The image pixel arrays and evaluation results can be archived onto a floppy disk by the personal computer.

The invention being claimed is:

1. A method of testing a specimen for resistance to abrasion, steps of which comprise:
    optically scanning the specimen prior to abrasion to produce a first array of pixels representing the specimen;
    abrading the specimen;
    optically scanning the specimen after the abrading to produce an second array of pixels representing the specimen;
    producing a plurality of difference values, each one of which indicates a degree of difference between corresponding pixels in the first and second arrays; and quantifying the abrasion of the specimen from the plurality of difference values.

2. The method as recited in claim 1 wherein said step of abrading comprises:

placing either two specimens or a specimen and a receptor between block-like members having curved end surfaces to form a test assembly;

positioning the test assembly on a platform with the curved end surfaces of the block-like members abutting the platform; and vibrating the platform.

3. The method as recited in claim 1 wherein the step of quantifying the degree of abrasion comprises deriving an average magnitude of abrasion of the specimen.

4. The method as recited in claim 3 further comprising measuring thermal noise produced by a device that preforms the scanning steps; and wherein said step of quantifying the degree of abrasion includes correcting the average magnitude for the thermal noise.

5. The method as recited in claim 1 wherein the step of quantifying the degree of abrasion comprises deriving a mean square energy for abrasion of the specimen.

6. The method as recited in claim 5 further comprising measuring thermal noise produced by a device that preforms the scanning steps; and wherein said step of quantifying the degree of abrasion includes correcting the mean square energy for the thermal noise.

7. The method as recited in claim 5 wherein the step of quantifying the degree of abrasion comprises deriving average voltage for abrasion of the specimen.

8. The method as recited in claim 3 wherein the step of quantifying the degree of abrasion comprises:

selecting different groups of difference values with each group associated with a region of the second pixel array; and for each group of difference values, deriving a value for one or more parameters selected from the group consisting of average magnitude of abrasion, mean square energy of abrasion, and average voltage of abrasion.

9. The method as recited in claim 1 further comprising employing results of the quantifying step to create a contour map of the specimen in which areas of differing degrees of abrasion are denoted.

10. A method of testing a specimen for resistance to abrasion, steps of which comprise:

optically scanning the specimen prior to abrasion to produce an first array of pixels having a foreground section representing the specimen and a background section;

abrading the specimen;

optically scanning the specimen after to abrasion to produce an second array of pixels having a foreground section representing the specimen and a background section;

creating a process window within the foreground section of one of the first and second pixel arrays;

producing a plurality of difference values, each one of which indicates a degree of difference between a pixel within the process window in one array and a corresponding pixel in the other array;

defining at least one region of the second array; and for each defined region, deriving a value for one or more parameters selected from the group consisting of average magnitude of abrasion, mean square energy of abrasion and average voltage of abrasion.

11. The method as recited in claim 10 further comprising correcting the first and second arrays of pixels for effects of a non-uniform response of a device that optically scans the specimen.

12. The method as recited in claim 10 further comprising a step of registering the first and second pixel arrays prior to producing a plurality of difference values.

13. The method as recited in claim 10 wherein the step of registering the first and second pixel arrays comprises:

locating margins of the foreground section of the first array of pixels;

locating margins of the foreground section of the second array of pixels; and shifting pixels in one of the first and second arrays of pixels so that the margins of the foreground section of the first array are aligned with the margins of the foreground section of the second array.

14. The method as recited in claim 10 further comprising employing the derived parameters for each region to create a contour map of the specimen in which areas of differing degrees of abrasion are denoted.

15. The method as recited in claim 10 further comprising selecting material of the specimen for a particular use based upon derived values for the selected parameters.

16. An apparatus for analyzing abrasion of a specimen comprising:

a scanner that produces an image of the specimen which image is formed by an array of pixels, each pixel having a digital signal level;

a digital memory connected to said scanner to contain a first array of pixels representing a first image of the specimen prior to abrasion and a second array of pixels representing a second image of the specimen after to abrasion;

a mechanism which defines a process window that identifies pixels to be analyzed within the first and second arrays;

a comparator, coupled to said memory, which for the pixels identified by the process window derives a value for a difference between the digital signal level a pixel in the first array and the digital signal level of a corresponding pixel in the second array; and a evaluator which employs a plurality of difference values received from said comparator to quantify the abrasion of the specimen.

17. The apparatus as recited in claim 16 further comprising means for shifting one of the first and second arrays of pixels to register representations of the specimen in the first and second images.

18. The apparatus as recited in claim 16 further comprising another mechanism that measures a non-uniformity of a response to light of said scanner; and a means, connected to said memory, for correcting the pixels in the first and second arrays for that non-uniformity.

19. The apparatus as recited in claim 16 wherein said evaluator derives from the difference values one or more of an average magnitude of abrasion, a mean square energy of abrasion, and average voltage of abrasion.

20. The apparatus as recited in claim 19 further comprising a mechanism that measures thermal noise produced by said scanner; and a mechanism that corrects the average magnitude of abrasion and the mean square energy of abrasion for the thermal noise.

* * * * *